(12) United States Patent
Laugharn, Jr. et al.

(10) Patent No.: US 10,058,860 B2
(45) Date of Patent: Aug. 28, 2018

(54) METHODS AND APPARATUSES FOR ACOUSTIC TREATMENT OF SAMPLES

(71) Applicant: Covaris, Inc., Woburn, MA (US)

(72) Inventors: James A. Laugharn, Jr., Winchester, MA (US); Gregory J. Kellogg, Cambridge, MA (US)

(73) Assignee: Covaris, Inc., Woburn, MA (US)

( * ) Notice: Subject to any disclaimer, the term of this patent is extended or adjusted under 35 U.S.C. 154(b) by 554 days.

(21) Appl. No.: 14/817,518

(22) Filed: Aug. 4, 2015

(65) Prior Publication Data
US 2016/0038932 A1    Feb. 11, 2016

Related U.S. Application Data

(60) Provisional application No. 62/033,413, filed on Aug. 5, 2014.

(51) Int. Cl.
| | | |
|---|---|---|
| *B01L 3/00* | (2006.01) | |
| *G01N 1/40* | (2006.01) | |
| *G01N 1/28* | (2006.01) | |
| *G01N 1/44* | (2006.01) | |

(52) U.S. Cl.
CPC ............. *B01L 3/502* (2013.01); *G01N 1/286* (2013.01); *G01N 1/44* (2013.01); *B01L 2300/045* (2013.01); *B01L 2300/0832* (2013.01); *B01L 2300/14* (2013.01); *B01L 2400/0439* (2013.01); *B01L 2400/0478* (2013.01)

(58) Field of Classification Search
CPC ................. B01L 3/502; B01L 2300/14; B01L 2300/045; B01L 2300/0832; B01L 2400/0478; B01L 2400/0439; G01N 1/286; G01N 1/44

See application file for complete search history.

(56) References Cited

U.S. PATENT DOCUMENTS

| | | |
|---|---|---|
| 6,719,449 B1 | 4/2004 | Laugharn, Jr. et al. |
| 6,948,843 B2 | 9/2005 | Laugharn, Jr. et al. |
| 8,459,121 B2 * | 6/2013 | Laugharn, Jr. ...... B01F 11/0283 73/64.53 |
| 9,126,177 B2 * | 9/2015 | Laugharn, Jr. ...... B01F 11/0283 |
| 9,918,694 B2 * | 3/2018 | Laugharn, Jr. ........... A61B 8/00 |
| 2008/0031094 A1 | 2/2008 | Laugharn, Jr. et al. |

(Continued)

*Primary Examiner* — Daniel Pihulic
(74) *Attorney, Agent, or Firm* — Wolf, Greenfield & Sacks, P.C.

(57) ABSTRACT

A treatment vessel may allow a user, or automated system, to manipulate sample material within a treatment area during processing (e.g., focused acoustic treatment), as well as subject the sample material to a staged processing protocol. The vessel may include openings for receiving/discharging the sample material. Walls within the vessel may be movable between various positions, to permit or obstruct flow of sample material into or out from a treatment area. The wall(s) may push the sample material within the vessel, as well as adjust pressure levels within the treatment area. In some embodiments, an acoustic treatment system may include a flexible coupling medium that may be deformed toward the vessel upon an application of suitable pressure thereto. When the medium presses up against the vessel, defects (e.g., particles, bubbles, interfaces, etc.) that may otherwise be present along the acoustic wave path may be reduced.

51 Claims, 12 Drawing Sheets

(56) References Cited

U.S. PATENT DOCUMENTS

2015/0105750 A1   4/2015  Laugharn, Jr. et al.
2015/0161982 A1   6/2015  Laugharn, Jr. et al.
2016/0038932 A1*  2/2016  Laugharn, Jr. .......... B01L 3/502
                                                   435/173.7

* cited by examiner

METHODS AND APPARATUSES FOR ACOUSTIC TREATMENT OF SAMPLES

CROSS REFERENCE TO RELATED APPLICATION

This application claims the benefit of U.S. Provisional Application Ser. No. 62/033,413, filed Aug. 5, 2014, which is hereby incorporated by reference in its entirety.

BACKGROUND

Acoustic energy-based sample processing devices, such as Adaptive Focused Acoustic apparatuses made by Covaris of Woburn, Mass., are effective for homogenization, lysing, disruption or other processing of biological tissues, cells and other sample material. The devices are also beneficial for chemical applications, such as compound dissolution, formulation, micronization, emulsification and other processes.

SUMMARY

The present disclosure relates to focused acoustic processing of sample materials (e.g., biological tissues/cells, chemical formulations, etc.). The inventor has recognized that it would be beneficial to be able to move, compress, expand or otherwise manipulate sample material within a treatment vessel, which may allow the sample material, and derivatives thereof, to be subjected to a sequence of processing conditions (e.g., combination of temperature, pressure, exposure to a certain degree of focused acoustic energy, etc.). Depending on the type of sample material and desired treatment, a treatment vessel may be configured to accommodate entry of the sample material therein, and the vessel may also be configured to suitably isolate the sample material from the outside environment. Further, the vessel may be configured to manipulate or cause movement of the sample material within an internal volume of the vessel.

In some embodiments, the vessel includes one or more openings (e.g., located at a top side of the vessel) for receiving sample material into a chamber, or discharging sample material therefrom. In some cases, the chamber may extend in a lateral direction to accommodate movement therein. One or more walls within the chamber may be movable (e.g., multiple walls able to move in cooperation, along a lateral direction) between a first position, to permit flow of sample material into or out from a treatment area of the vessel, and a second position, to obstruct flow of sample material into or out from the treatment area. The movable wall(s) may also be configured to cause the sample material to move or slide within the chamber, and/or to adjust a pressure level within the treatment area. Accordingly, the vessel may allow for the sample material contained therein to be appropriately manipulated within a treatment area, for example, while simultaneously exposed to focused acoustic energy.

In some embodiments, an acoustic treatment system may include a coupling medium arranged to transmit acoustic energy from an acoustic energy source to a vessel. The coupling medium may be flexible such that a portion of the coupling medium may be deformed toward the vessel upon an application of suitable pressure to the coupling medium. For example, the coupling medium may be deformed so as to press up against the vessel, minimizing or otherwise reducing the number of defects (e.g., particles, bubbles, interfaces, etc.) that may be present along the path through which the acoustic energy travels. Such defects, when present, may cause disruption of the acoustic energy wave, which may, in turn, diminish the overall effect(s) of the acoustic energy on the sample material.

Acoustic energy may be arranged or provided in any suitable way, e.g., defining a focal zone that at least partially overlaps the sample and is sufficient to cause at least one of lysing, extraction, permeabilizing, stirring, catalyzing, degrading, fluidization, heating, particle breakdown, nucleic acid shearing, sterilization, or disruption of molecular bonds in the sample. In some embodiments, the acoustic energy source is spaced from and exterior to the vessel so that at least a portion of the acoustic energy propagates exterior to the vessel, and the acoustic energy comprises a frequency of between about 100 kilohertz and about 100 megahertz and a focal zone having a width of less than about 2 centimeters.

In an illustrative embodiment, a vessel for treating a material is provided. The vessel includes a chamber defining an internal volume for containing a sample material and accommodating passage of the sample material to a treatment area. The vessel includes at least one opening for receiving an inflow of sample material into the treatment area or for discharging an outflow of material from the treatment area. The vessel also includes a first wall movable within the internal volume of the chamber; and a second wall movable within the internal volume of the chamber, wherein the first and second walls, in cooperation, are adapted to cause the sample material to move within the internal volume and to adjust a pressure within the treatment area.

In another illustrative embodiment, a vessel for treating a material is provided. The vessel includes a chamber defining an internal volume for containing a sample material and accommodating passage of the sample material to a treatment area, the chamber having a top side and extending in a lateral direction. The vessel includes at least one opening located at the top side of the chamber; and at least one wall movable within the internal volume of the chamber, configured for movement along the lateral direction between a first position to permit flow of sample material into or out from the treatment area and a second position to obstruct flow of sample material into or out from the treatment area.

In a further illustrative embodiment, a method of treating a material with acoustic energy is provided. The method includes causing flow of sample material into an internal volume of a chamber; moving a first wall and a second wall in cooperation within the internal volume of the chamber to cause the sample material to move within the internal volume and to adjust pressure within a treatment area; treating sample material located within the treatment area with acoustic energy having a frequency of about 100 kHz to 100 MHz and a focal zone of acoustic energy in the treatment area, the acoustic energy transmitted from an acoustic energy source to the chamber through a coupling medium held in a vessel; and causing flow of the treated sample material away from the internal volume of the chamber.

In yet another illustrative embodiment, a system for acoustically treating a material is provided. The system includes a vessel holder for holding a vessel having a chamber defining an internal volume for containing a sample material. The system further includes an acoustic energy source arranged to be spaced from the vessel and adapted to emit acoustic energy having a frequency of about 100 kHz to 100 MHz to create a focal zone of acoustic energy in the internal volume. The system includes a flexible coupling medium arranged to transmit acoustic energy from the acoustic energy source to the vessel and adapted for at least a portion to be deformed toward the vessel upon pressure application.

In another illustrative embodiment, a method of treating a material with acoustic energy is provided. The method includes deforming a flexible coupling medium toward a vessel location; positioning a vessel having a chamber defining an internal volume for containing a sample material at the vessel location; and transmitting acoustic energy having a frequency of about 100 kHz to 100 MHz from an acoustic energy source through the coupling medium to form a focal zone of acoustic energy within the internal volume.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to illustrative embodiments shown in the drawings, in which like numerals reference like elements, and wherein.

DETAILED DESCRIPTION

Figure 1:
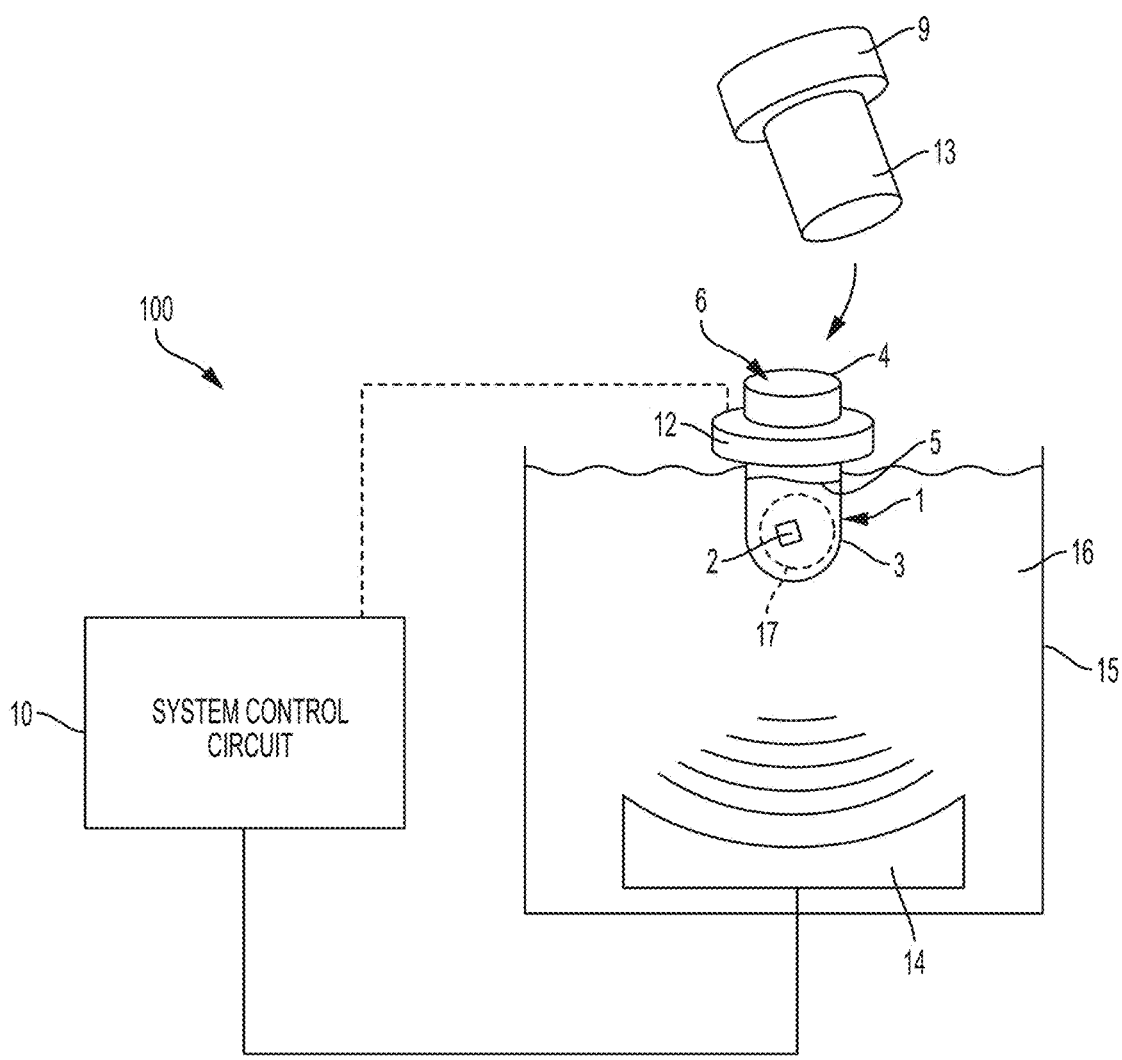
FIG. 1 shows a schematic block diagram of an acoustic treatment system that incorporates one or more aspects of the present disclosure.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, aspects of the present disclosure may be used alone or in any suitable combination with each other. Thus, the phraseology and terminology used herein is for the purpose of description and should not be regarded as limiting.

As described herein, suitable acoustic treatment systems may be used to treat sample material with focused acoustic energy, in a desirable manner. Examples of such acoustic treatment systems and control arrangements are described in U.S. Pat. Nos. 6,948,843 and 6,719,449, assigned to Covaris of Woburn, Mass.

The inventor has appreciated that focused acoustic processing may be particularly effective or otherwise beneficial, when performed under controlled conditions. For instance, subjecting a sample material held within a vessel to focused acoustic treatment while under a pressure different (e.g., greater, lower) than that of the outside ambient environment may lead to enhanced processing throughput and/or efficacy (e.g., greater power/energy delivered to the sample material). This increased efficacy may provide improved results (e.g., improved cell lysis, mixing, fragmentation, homogenization, sterilization, etc.), as compared to if the sample material is treated under ambient conditions (e.g., atmospheric pressure).

Aspects of the present disclosure allow a user to control the manner in which sample material is processed (e.g., during acoustic treatment). For instance, a vessel that is constructed to receive sample material within an internal volume, or treatment area associated with the internal volume, may be able to be manipulated by a user or automated system to move, compress and/or expand the sample material, or treatment area within which the sample material is located, in a suitable manner (e.g., under an appropriate seal). Such manipulation may be provided in conjunction with a sample treatment protocol, such as focused acoustic processing or other type of processing. In some embodiments, to prepare the sample material for treatment, the volume within which the sample material is located (e.g., a treatment area) may be compressed or otherwise subject to a compressive force, so as to increase the overall pressure of the sample material.

For certain embodiments, when focused acoustic energy is applied to a sample while under high pressure, or pressure greater than ambient pressure levels, the desired result may be obtained in a shorter period of time and/or may result in improved output quality (e.g., greater degree of sterilization, fragmentation, lysis, mixing, homogenization, etc. of the sample). In various embodiments, an air-tight seal is formed between an interior space of the vessel and the outside environment, to permit pressurization of the interior space of the vessel relative to the surrounding atmosphere. Various systems and methods for pressurizing an interior space of a vessel are described in U.S. Publication No. US2008/0031094, entitled "Methods and apparatus for treating samples with acoustic energy," and U.S. Provisional Application No. 61/890,894, entitled "Apparatus and Method for Acoustic Treatment and Delivery of Samples for Medical Treatment," aspects of each of which may be used in association with aspects of the present disclosure. In addition, other techniques and systems are described herein for pressurizing a sample volume during acoustic treatment.

As discussed herein, the conditions (e.g., higher than atmospheric pressure, approximately 4 degrees C. or 37 degrees C., etc.) under which samples are subject to focused acoustic processing may contribute to the overall effectiveness of the acoustic treatment. In some embodiments, a sample to be treated using focused acoustics is contained within an interior volume, or treatment area within the interior volume, defined by a chamber of a vessel.

The treatment area that contains the sample, or the sample itself, may be pressurized to a pressure substantially greater than that of the surrounding environment. For example, if the pressure of the surrounding environment is 1 atm, then the pressure of the treatment area of the vessel that contains the sample material may be increased to a pressure of greater than 1 atm, greater than 2 atm, greater than 3 atm, greater than 4 atm, greater than 5 atm, greater than 7 atm, greater than 10 atm, or between 1 atm and about 10 atm, between about 2 atm and about 8 atm, or between about 3 and about 6 atm.

In addition to an overpressure within the interior space, or treatment area, of the vessel, a headspace above the sample may also be reduced and/or maintained for effective acoustic treatment. In some embodiments, the headspace above the sample within the interior space of the vessel may be 50% or less of the sample volume. In some embodiments, the headspace may be 20% or less of the sample volume, 10% or less of the sample volume, 5% or less of the sample volume, 3% or less of the sample volume, 2% or less of the sample volume, 1% or less of the sample volume, or e.g., as low as 0% of the sample volume.

In various embodiments, combined conditions of pressure, temperature and/or reduced headspace within the interior space of the vessel may provide for both higher power and more efficient treatment of the sample than if the pressure, temperature and/or headspace conditions are absent.

FIG. 1 shows a schematic block diagram of an acoustic treatment system 100 that incorporates one or more aspects of the embodiments described herein. It should be understood that although embodiments described herein may include most or all aspects of the present disclosure, certain aspects may be used alone or in any suitable combination with other aspects of other embodiments.

In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. In this example, the vessel 4 is a standard rimless 13×100 mm borosilicate glass test tube, but it should be understood that the vessel 4 may have any suitable shape, size, material, or other feature, as further described herein. The vessel 4 may be formed of glass, plastic, metal, composites, and/or any suitable combinations of materials, and formed by any suitable process, such as molding, machining, extrusion, stamping, and/or a combination of processes. In some embodiments, the vessel 4 may have an interior space that is suitable to accommodate an overpressure, i.e., a pressurized state where the pressure within an interior space of the vessel is greater than the pressure of the environment exterior to the vessel. Various embodiments of vessels in accordance with the present disclosure are described further below.

The acoustic treatment system 100 may also include a coupling medium container 15 that is capable of holding a medium 16 (such as water or other liquid, deformable/flexible medium, gas, gel, solid, semi-solid, and/or a combination of such components) which transmits acoustic energy from the transducer 14 to the vessel 4. In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silicone material), which is also attached to a vessel holder 12, which may be formed, at least in part, by an opening or other feature of the medium 16. Thus, the transducer 14, medium 16 and holder 12 may be formed as a single integrated part, if desired.

In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. In addition, or alternatively, the transducer 14 may form the focal zone 17 so that the focal zone 17 is suitably positioned relative to the sample 1 or vessel 4.

Or, in some embodiments, the coupling medium may be flexible such that a portion of the coupling medium may be deformed toward the vessel upon appropriate actuation of the coupling medium. For example, the coupling medium may be pressurized so as to be deformed, resulting in the coupling medium pressing up against the vessel. Such deformation and/or pressing against the vessel may reduce the overall number of defects (e.g., particles, bubbles, interfaces, etc.) that may otherwise be present along the path through which the acoustic energy travels.

To control the acoustic transducer 14, the acoustic treatment system 100 may include a system control circuit 10 that controls various functions of the system 100 including operation of the acoustic transducer 14 and/or other aspects (e.g., temperature, pressure, etc.). For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signal(s) for the transducer 14 to produce desired acoustic energy.

As discussed in more detail below, the system control circuit 10 may control various other acoustic treatment system 100 functions, such as positioning of the vessel 4 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

As noted above, in various embodiments, the system control circuit 10 may control other aspects of the acoustic treatment system 100, such as temperature and/or pressure within a treatment area. For example, a thermal adjustment apparatus (e.g., Peltier cooling chamber, thermal control jacket, coolant circulation system, etc.) may be provided with the coupling medium 16 and/or vessel 4, for controlling the temperature of the sample material 1 and/or coupling medium 16. In addition, a pressure adjustment apparatus (e.g., gas feed, compressive block, pistons, plungers, springs, etc.) may also be provided so as to apply a suitable amount of pressure to the sample material 1 and/or coupling medium 16. Accordingly, the control circuit 10 may monitor the temperature and/or pressure of various parts of the system (e.g., coupling medium, vessel) and adjust the appropriate parameter(s) as desired.

In this illustrative embodiment, the sample 1 includes a solid material 2 and a liquid 3, e.g., 100 milligrams of a biological sample material in 1 milliliter of distilled water.

Of course, those of skill in the art will appreciate that the sample 1 is not limited to a solid material 2 in a liquid 3, as the sample 1 may take any suitable form, such as a liquid only form, a solid only form, a mixture of liquid and solid as in this embodiment, a gel, a semi-solid, a gas, and/or combinations thereof. Samples may include any suitable material(s), such as biological materials (e.g., proteins, liposomes, nucleic acids, antibiotics, steroids, bioactive agents, cells, etc.).

An interface 5 separates the sample 1 from the headspace 6, which is shown to be a gaseous region immediately above the sample 1. For some power levels at the focal zone 17 and/or sample types or arrangements, acoustic energy suitable to cause mixing, e.g., lysing, extraction, permeabilizing, catalyzing, degrading, fluidization, heating, particle breakdown, sterilization, shearing and/or disruption of molecular bonds in the sample 1, may also cause portions of the sample 1 (including solid material 2 and/or liquid material 3 of the sample 1) to be splashed or otherwise ejected from the interface 5. In some cases, the ejected sample 1 may return to the main volume of sample 1, but in other cases, the ejected sample 1 may adhere to the vessel 4 above the interface 5 or otherwise fail to return to the main sample 1. In either case, the ejected sample 1 may spend a reduced amount of time in the focal zone 17.

As discussed further herein, a vessel may include movable walls that allow for appropriate adjustment of the treatment area. For example, such movable walls may adjust the location, volume and/or force applied to the treatment area, and/or the amount of headspace available for the sample located within treatment area during focused acoustic processing. In some embodiments, the walls may move toward one another, or one wall may move toward another wall, in a manner that reduces the overall amount of headspace, or volume containing the sample, within the treatment area. In some cases, the headspace may be minimized or otherwise reduced to enhance the effect(s) of focused acoustic treatment, for example, by increasing the amount of time that the sample is physically located within the focal zone.

In addition, or alternatively, acoustic energy may cause gas in the headspace 6 to be entrained into the sample 1, such as by dissolving a portion of the gas in the headspace 6 and/or by capturing bubbles of headspace gas in the sample due to motion of the liquid at the interface 5. As discussed herein, gas located within the sample 1 may interfere with acoustic energy, such as by the presence of gas bubbles or other interfacial defects at or near the focal zone 17, reflecting acoustic energy away from the sample 1 and/or by dissolved gas increasing a pressure in cavitation bubbles created by acoustic energy, thereby decreasing the rate or force at which the cavitation bubbles collapse. In some cases, gas bubbles or other interfacial defects located within the coupling medium may also interfere with the overall effectiveness of acoustic treatment.

Without wishing to be bound by theory, the collapse of cavitation bubbles may transfer significant kinetic energy to sample materials, causing the materials to be lysed, sheared or otherwise mechanically operated on. By increasing a pressure in such bubbles, dissolved gas in the sample may result in a reduction in the energy released by cavitation bubble collapse, reducing an effectiveness of acoustic treatment.

In accordance with some embodiments of the present disclosure, a headspace at an interface of a sample can be controlled, e.g., in volume and/or surface area presented at the interface, to reduce an amount of gas available for entrainment in the sample. Headspace size (volume and/or surface area presented at the interface 5) can be controlled in a variety of different ways. For example, a cap 9 may be engaged with the vessel 4 so as to position a headspace control member 13 near the interface 5. In this embodiment, the headspace control member 13 is attached to the cap 9 (e.g., formed as a unitary part with the cap 9), but other arrangements are possible, as discussed more below. The headspace control member 13 may reduce a volume of the headspace 6 to be 50% or less (e.g., 20% or less, 10% or less, 5% or less, 2% or less, 1% or less) than the volume of the sample. In some embodiments, the volume of the headspace 6 may be 10% or less than the volume of the sample 1, even as little as 0% of the sample volume where the headspace control member 13 is in contact with the sample 1 at the interface 5.

In another aspect of the present disclosure, a treatment vessel may be arranged so as to adjust certain conditions under which sample material is processed during treatment. For example, the treatment vessel may be constructed to receive sample material into a treatment area, and allow for movement of the sample material and/or adjustment of pressure thereof during treatment (e.g., exposure to focused acoustic energy, radiation, etc.). When treatment of the sample material is finished, the vessel may also be constructed to accommodate discharge of the sample material therefrom, and delivery to another location (e.g., for further processing, packaging, disposal, etc.).

Figure 2:
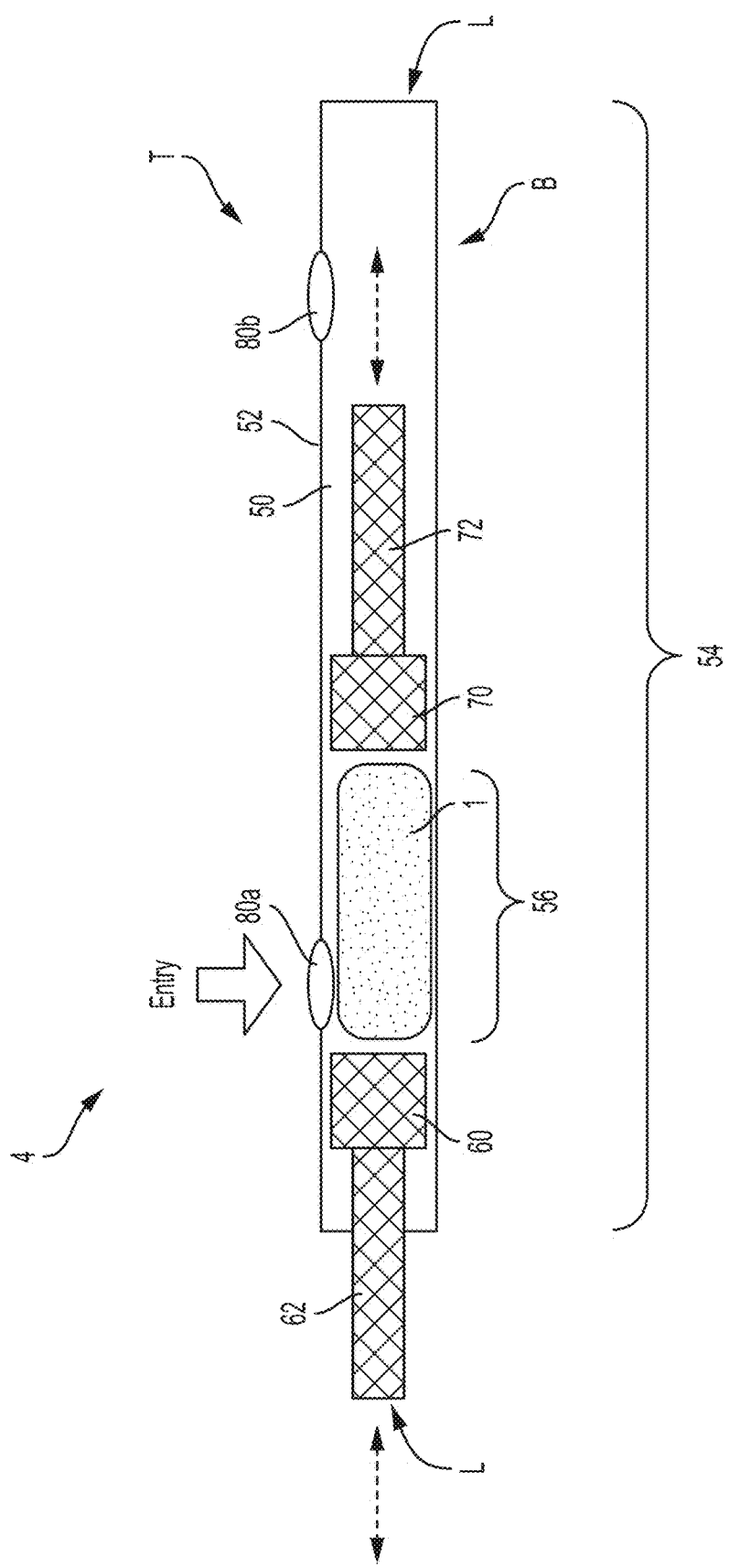
FIG. 2 depicts a schematic of a cross-sectional view of a vessel in accordance with an embodiment.
Figure 3:
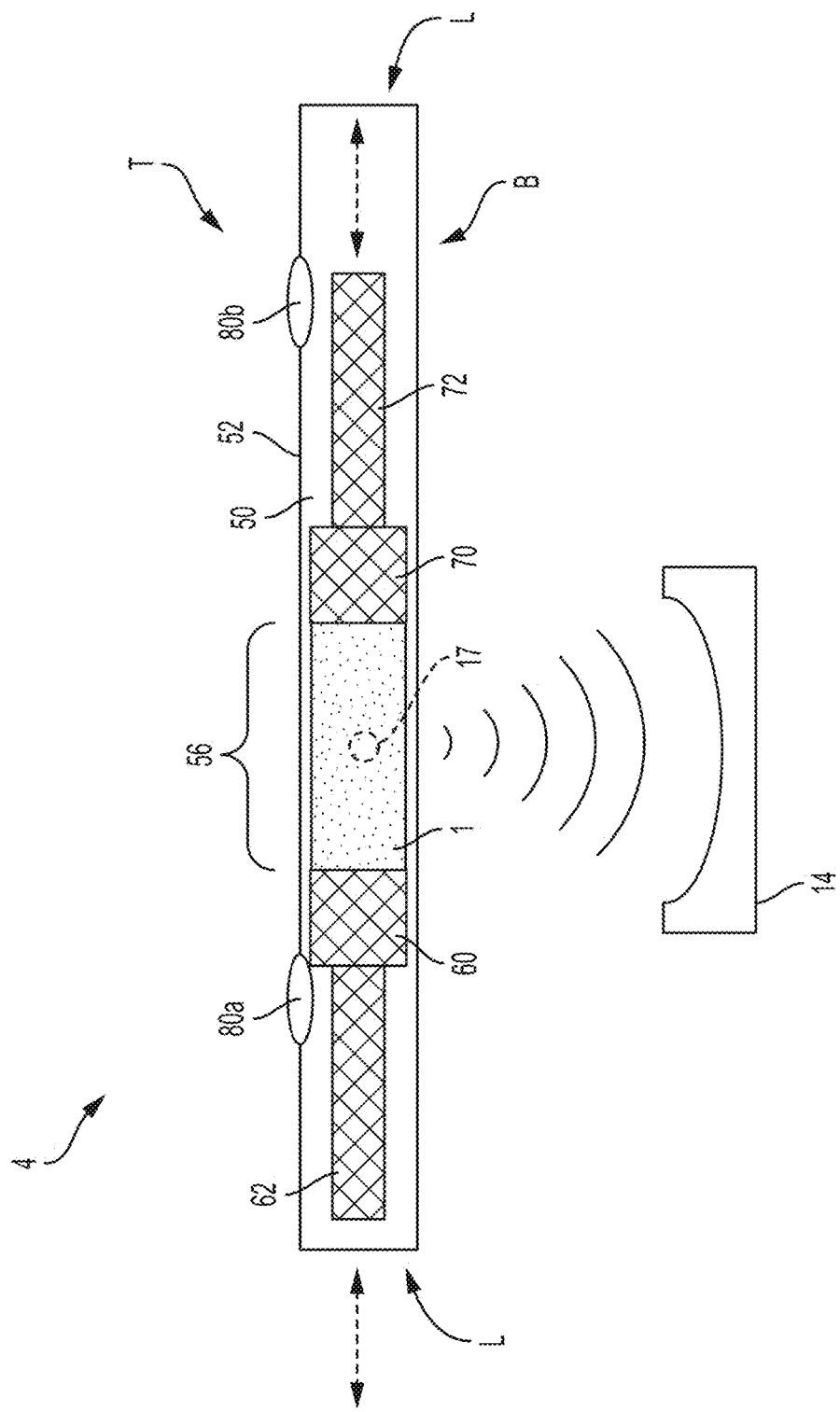
FIGS. 3-4 illustrate the vessel of FIG. 2 in use.
Figure 4:
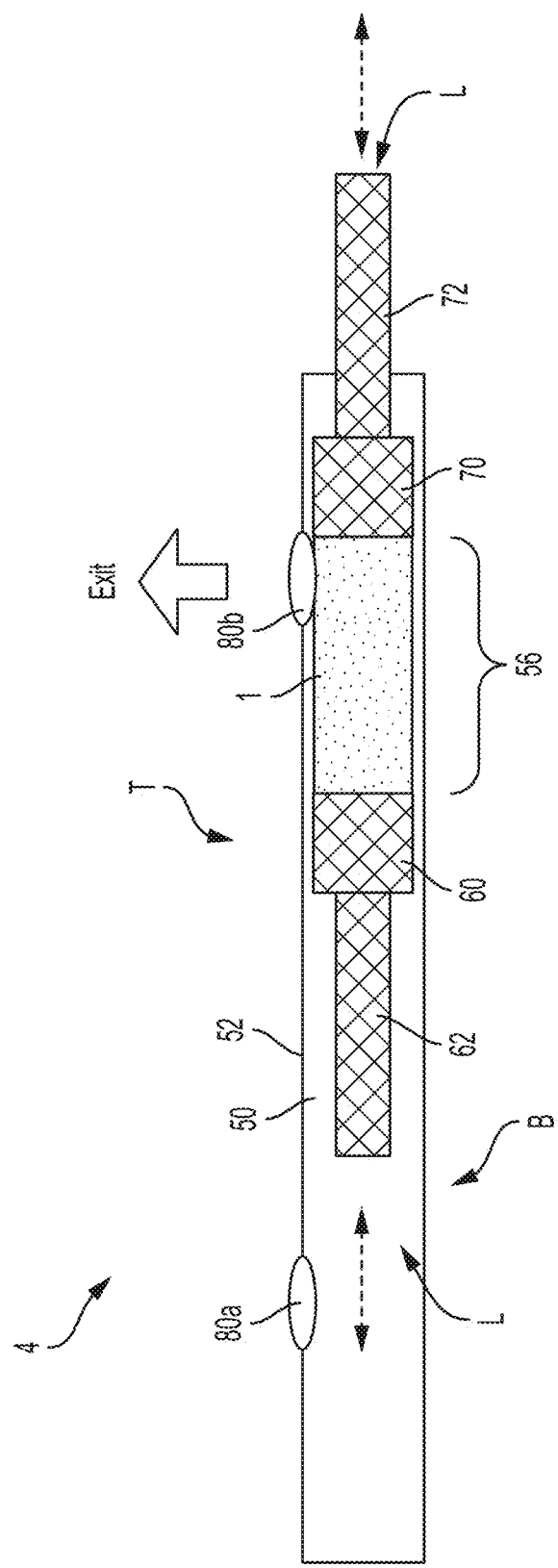

FIGS. 2-4 show an illustrative embodiment of a vessel 4 having a chamber 50 that includes an inner wall 52 that defines an internal volume 54 of the vessel. The vessel 4 (and chamber 50) may have any suitable shape, such as a cylindrical contour having a circular cross section, or a substantially rectangular, polygonal, ellipsoidal or oblong cross section. In some embodiments, the vessel 4 may have a polyhedral shape (e.g., rectangular prism, cuboid, etc.). Or, in some embodiments, the vessel 4 has a substantially flat and/or elongated configuration where at least a portion thereof may extend laterally along an appropriate plane and/or axis.

The internal volume of the vessel chamber may have any suitable dimensions. For example, the length of the chamber may be between 1 mm and 50 mm, between 1 mm and 40 mm, between 2 mm and 30 mm, between 5 mm and 20 mm, or between 10 mm and 15 mm (e.g., approximately 10 mm). Or, the width of the chamber may be between 0.1 mm and 10 mm, between 0.1 mm and 5 mm between 0.5 mm and 3 mm, or between 1.0 mm and 2.0 mm (e.g., approximately 1.0 mm).

In this embodiment, the vessel 4 includes movable walls 60, 70 located on opposing sides of the vessel and shaped to conform to the dimensions of the chamber wall 52. For example, the exterior surface of the movable walls 60, 70 may be shaped to be slightly smaller than the interior surface of the chamber wall 52, so that one or both of the walls 60, 70 are able to move through the chamber 50. In some cases, sealing members (not shown in FIGS. 2-4), such as o-rings, gaskets, elastomeric material, etc., may further be provided at the ends of the movable walls 60, 70 to prevent undesirable leakage of material past the walls, while allowing movement of the wall(s) through the chamber. One or both of the walls 60, 70 may be movable with respect to the chamber 50, within the internal volume 54, for example, along a lateral or substantially horizontal direction of the chamber. For instance, as shown in FIGS. 2-4, the walls 60, 70 may be moved, separately controlled, back and forth along a lateral direction, as indicated by the dotted double arrows.

In this embodiment, the space between the walls 60, 70 provides a treatment area 56 within which sample material may be contained and processed. Accordingly, the walls 60, 70 may be moved in cooperation, separately or in concert, to slide the sample material to an appropriate location within the vessel for treatment thereof.

In some embodiments, the wall(s) may provide an obstruction or, in some cases, a barrier to fluid flow therethrough and/or there around. For example, the wall(s) may be substantially impermeable to flow of fluid. Though, for some embodiments, it may not be necessary for the wall(s) to be impermeable to fluid flow. That is, in some cases, the wall(s) may be at least partially or selectively permeable to fluid flow therethrough. For example, the wall(s) may include a semi-permeable membrane that permits gas, liquid and molecules smaller than a certain size threshold to pass through.

Besides one or more movable walls being selectively permeable, other non-movable portions of the chamber wall may also be selectively permeable. For example, the chamber wall may have a selectively permeable region, or filter, that only allows certain compositions to pass therethrough. In this respect, translation of a movable wall such that the sample moves over the selectively permeable region of the chamber wall may result in fluid exchange of certain parts of the sample through the selectively permeable region.

In some embodiments, positioning the sample over a selectively permeable region of the chamber wall may serve to drive excess gas out from the sample. As a result, removal of excess gas from the sample may lend the sample to more efficient processing when exposed to focused acoustic energy.

The outer edge of the wall(s) 60, 70 and the inner wall 52 of the chamber 50 may be arranged to form a seal upon mutual contact. In certain embodiments, the outer edge of the wall(s) 60, 70 may include an elastomeric material (e.g., rubber, silicone, relatively soft plastic, etc.) and the inner wall 52 of the chamber 50 may include a suitable complementary material, such as a relatively rigid material (e.g., glass, metal, kapton, relatively hard plastic, etc.) so as to obstruct fluid from flowing past the wall(s) 60, 70. As noted above, for some embodiments, the outer edge of the movable wall(s) 60, 70 includes a silicone or elastomeric O-ring that, when appropriately fitted with the wall(s) 60, 70 and the chamber wall 52, is able to form a sealed engagement therebetween. Though, it can be appreciated that, for some embodiments, the inner wall 52 of the chamber 50 is composed of a material that is relatively compliant.

In various embodiments, a movable wall may, effectively, include a piston, plunger, sealing member, or other suitable structural feature. The wall(s) 60, 70 may include respective handles 62, 72, or one or more other features that allows each wall to be manipulated in a suitable manner. For example, a user and/or automated apparatus (e.g., robot) may grasp or otherwise couple with one or both of the handles 62, 72 so as to suitably move the handle(s) back and forth along the lateral direction of the vessel 4.

As shown in the figures, the cross-sectional area of the handle(s) is less than that of the portion of the wall(s) that engages with the inner wall of the chamber. Such an arrangement allows for fingers, graspers, tongs or other grasping mechanism(s) to appropriately reach into the vessel so as to move or otherwise manipulate the wall(s). Any suitable handling feature(s) may be employed. For example, the wall(s) or handle(s) may include a small opening for receiving a protruding rod of an actuating device which, upon suitable engagement, may be used to move the wall(s) back and forth.

The movable walls 60, 70 of the vessel may include any suitable material. In some embodiments, the side of one or more of the walls facing the treatment area 56 includes a hydrophilic material which, in some instances, may be helpful to enhance the results of focused acoustic processing, or other suitable types of processing. For example, in some cases, a wall having a relatively hydrophilic surface may be more effective to repel components (e.g., cellular components, molecules, etc.) of a biological solution, or otherwise prevent adsorption, as compared to a hydrophobic surface, or surface that is not hydrophilic. Alternatively, the side of one or more of the walls facing the treatment area includes a hydrophobic material. Biological components of the solution that are less likely to accumulate at the surface of the movable wall(s) may be exposed to a greater degree of focused acoustic energy than would otherwise be the case. Or, the wall(s) may include a material that effectively lowers the threshold of cavitation upon exposure to focused acoustic energy. Accordingly, the wall(s) may provide one or more nucleation sites for acoustic cavitation.

In some embodiments, the movable walls 60, 70 can be moved in cooperation, separately and/or in concert, so as to control fluid flow into or out of a treatment area 56, and also movement of fluid therein. As shown in FIGS. 2-4, the treatment area 56 may be provided as a controlled space of the internal volume 54 located between the movable walls 60, 70. In various embodiments, the wall(s) may be moved to a first position that permits flow of sample material 1 into or out from the treatment area 56 and, hence, the internal volume 54. The first position may involve positioning and/or orientation of the walls 60, 70 such that the treatment area 56 is accessible to fluid flow thereto and/or therefrom, for example, through an opening, channel, or other suitable fluid connection.

The wall(s) may also be moved to a second position so as to obstruct flow of sample material into or out from the treatment area 56. Accordingly, in this position, the walls 60, 70 may be oriented such that the treatment area 56 is fluidly inaccessible with the external environment.

The wall(s) 60, 70 may also be movable so as to cause the sample material to move within the chamber and/or to adjust pressure within the treatment area. For example, the wall(s) may be moved in concert within the internal volume 54, and kept at substantially the same distance apart from one another, resulting in movement of the treatment area 56 and the sample material located therein. Or, the wall(s) may be moved toward one another, resulting in compression of the sample material and/or a volume reduction of the treatment area, imparting the sample with a pressure that is greater than the surrounding pressure external to the vessel.

Alternatively, the wall(s) may be moved apart from one another, resulting in a volume expansion of the treatment area. In this case, the resulting pressure of the sample may be less than the surrounding pressure external to the vessel. In some embodiments, movement, volume reduction and/or volume expansion of the treatment area and, hence, the sample material, may occur while the wall(s) are in the second position, where flow of the sample material is confined to within the treatment area.

In some embodiments, the wall(s) that are permeable to fluid or gas flow therethrough may move toward one another without substantially affecting the pressure within the treatment area. For example, the wall(s) may move toward one another so as to reduce the amount of headspace within the treatment area. As noted above, reducing the amount of headspace within the treatment area during focused acoustic treatment may result in a greater degree of acoustic energy exposure to the sample than if the headspace were not reduced. Such an increase in acoustic exposure to the sample may, in turn, result in more effective, or efficient, acoustic processing. As noted above, for some embodiments, the wall(s) may be selectively permeable, for example, allowing gas to flow therethrough while confining liquid within the treatment area. Or, the movable wall(s) may cause the sample to be located within an area of the chamber where the chamber wall is selectively permeable, allowing certain components and/or fluid (e.g., gas) to pass through.

As further shown, the vessel 4 includes openings 80a, 80b for accommodating entry and/or exit of sample material to and from the internal volume 54 of the chamber 50 and the treatment area 54, when appropriate. Here, the openings 80a, 80b are located at a top side T of the vessel, although, one of skill would appreciate that each of the openings 80a, 80b may be located at any suitable location.

As discussed herein, a "top" side of the vessel refers to a region of the vessel based on a particular reference frame of the vessel, independent of the vessel orientation (e.g., tilted, upside down, sideways, etc.). As shown in FIGS. 2-4, the vessel 4 is oriented in a manner such that the openings are located at the top side T, opposite the bottom side B. However, if the vessel 4 is turned upside down, the openings are still considered to be located at the top side T, with respect to the reference frame of the vessel. In this embodiment, the only difference between the top side T and the bottom side B is that the top side T has openings, otherwise, the top and bottom sides are indistinguishable. However, in some embodiments, the top side T and the bottom side B of the vessel 4 may vary appropriately. For example, one or more openings may located at a suitable location along the top side T of the vessel and one or more other openings may be located at a suitable location along the bottom side B of the vessel. Or, in certain embodiments, one or more openings for accommodating entry and/or exit of sample material to and from the internal volume of the chamber may be located at a lateral side L of the vessel in addition to, or in place of, openings located at a top side T or a bottom side B of the vessel.

The vessel 4 may include any suitable number of openings. For example, vessels in accordance with various embodiments may have one or more openings (e.g., one opening, two openings, three openings, four openings, five openings, six openings, or more) for permitting flow of sample material into or out of the internal volume of the vessel chamber. In some embodiments, the vessel includes a single opening for accommodating both entry and exit of sample material into and out of the treatment area of the vessel.

In operation, as shown in FIG. 2, the movable walls 60, 70 are positioned on either side of the opening 80a, at the top side T of the vessel, so as to allow entry of sample material 1 through the opening 80a into the internal volume of the vessel chamber. Here, as discussed above, the treatment area for the sample material 1 is provided by the space located between the movable walls 60, 70, which are arranged so as to form a seal with the inner wall 52 of the chamber 50. In addition, in this particular embodiment, the walls 60, 70 are relatively impermeable to fluid flow therethrough, acting as a barrier that obstructs flow of sample material out of the treatment area. Accordingly, in this embodiment, the treatment area may move or otherwise be manipulated (e.g., enlarged/reduced in volume) based on how the walls 60, 70 are positioned.

As discussed above, the walls 60, 70 are movable (e.g., by application of an actuating force via respective handles 62, 72) along the lateral direction through which the chamber 50 extends, indicated by the dotted arrows. In FIG. 3, the wall 60 on one side of the vessel is moved toward the wall 70 on the other side of the vessel, past the opening 80a such that sample material is no longer able to flow into or out of the treatment area 56. While it may be possible for sample material to flow behind the wall(s) 60, 70 into or out of the internal volume 54 of the chamber, via openings 80a, 80b, in this position, the treatment area 56 is inaccessible.

At this point, the treatment area 56 may be further manipulated by the movable walls 60, 70. For example, the walls 60, 70 may be moved in cooperation so as to cause an adjustment in volume and/or pressure of the sample material 1. For example, movement of the walls 60, 70 toward one another may reduce the volume of the treatment area 56, hence, causing a reduction in sample volume. Accordingly, the compressive force to which the sample material is subjected results in an overall increase in pressure of the sample material. Conversely, movement of the walls 60, 70 away from one another may expand the volume of the treatment area 56 so as to expand the sample volume. As a result, the overall pressure of the sample material may be decreased.

In addition, the treatment area 56 may be subject to further processing or treatment. In some embodiments, and as shown in FIG. 3, the sample material 1, contained within the treatment area 56, is exposed to a suitable degree and amount of focused acoustic energy, as described herein. Any desired protocol for focused acoustic treatment may be employed, as the present disclosure is not limited in this respect. It can be appreciated that the treatment area 56 may be subject to other types of processing as well, such as radiative treatment(s) (e.g., UV, IR radiation exposure), thermal cycling, etc.

In some embodiments, the sample material may be subject to an appropriate treatment protocol while also being mechanically manipulated by the walls 60, 70. For example, the pressure of the sample material may be adjusted (e.g., increased, decreased) during an acoustic treatment. Or conversely, the walls 60, 70 may remain still, keeping the sample material in place, while the type of treatment to which the sample material is exposed is adjusted.

When it is desired for the sample material to be discharged from the vessel, as shown in FIG. 4, the walls 60, 70 may be further moved along the lateral direction through which the chamber extends such that the walls 60, 70 are positioned on either side of the opening 80b. As a result, the processed sample material 1 may then suitably flow out of the internal volume 54, hence, the treatment area 56.

While, in this example, the opening 80a is provided as an inlet and the opening 80b is provided as an outlet, it can be appreciated that the opening 80a may be employed as an outlet and the opening 80b may be used as an inlet, depending on the manner in which the walls 60, 70 are arranged. Or, in other embodiments, as also discussed above, a single opening may be used as both an inlet and an outlet through which sample material may flow into or out of the treatment area of the vessel. Or in further embodiments, more than two openings may be employed at suitable locations.

Vessels in accordance with embodiments described herein allow for the ability to easily modulate the parameters under which sample material is processed. In some embodiments, as discussed above, during focused acoustic treatment, the sample material may be simultaneously moved and/or the pressure of the sample material may be adjusted. For example, one or more parameters of the acoustic energy, temperature and/or pressure of the sample material may be adjusted based on the desired treatment outcome of the sample material.

Or, in some cases, the sample material may be processed using certain acoustic processing conditions while under a particular temperature and pressure, and at an appropriate point, it may be desirable to add additional sample material (e.g., buffer, reactant, biological material, chemicals, etc.) to the treatment area. Accordingly, the walls of the vessel may be positioned so as to permit the additional sample material(s) to be provided to the treatment area, when appropriate.

Processes that employ vessels in accordance with embodiments of the present disclosure may be performed manually or automatically. For example, a user, or system programmed to execute a series of instructions for processing the sample material, may hold the vessel and actuate the movable walls of the vessel so that the vessel receives a suitable amount of sample material into a treatment area. The movable walls may then be actuated so as to slide the sample material into a region of the vessel that allows for suitable processing thereof (e.g., pressure modulation, focused acoustic treatment, temperature adjustment, etc.), for example, away from the inlet/outlet opening(s) and optionally sealed from the external environment.

When appropriate, the movable walls may be further actuated so as to result in movement of the sample material to a region of the vessel that allows for exit of the processed sample material from the vessel and/or for entry of additional sample material therein, for further processing. It can be appreciated that any suitable combination of process steps may be employed, manually or automatically, based on the desired treatment protocol for the sample material.

In some embodiments, the vessel may be used to provide staged focused acoustic treatment to the sample material. For example, in preparing biological materials, such as cells, proteins, nucleic acids (e.g., DNA, RNA, etc.), or other appropriate materials, for subsequent analysis, isolation and/or purification, a suitable treatment protocol may be employed. That is, in some cases, focused acoustic processing under various parameters, in conjunction with other treatment conditions (e.g., pressure, temperature, exposure to suitable solvent/buffer/chemicals, etc.), may be appropriate.

In various embodiments, it may be desirable for individual molecules (e.g., nucleic acid molecules, proteins, etc.) of a certain size range to be extracted from a group of cells. In order for a relatively clean extraction to occur, an appropriate treatment protocol may be employed to deal with each stage of processing, such as for cell lysis, molecular bond disruption and isolation/purification.

For example, the vessel may accommodate flow of a solution of cells into the internal volume of the chamber, or treatment area between the movable walls, similar to that shown in FIG. 2. In some cases, a suitable number of nucleation materials (e.g., PTFE/glass, beads/rods, etc.), that suitably lower the cavitation threshold of the sample solution during acoustic treatment, may also be supplied to the treatment area, to better facilitate cellular lysis.

When the movable walls on either side of the treatment area are suitably positioned, similar to that shown in FIG. 3, the cell solution may be sealed off from the external environment for further processing. At this point, the solution may be subjected to high energy focused acoustics using parameters known to those of skill in the art for cellular lysis, under suitable conditions of temperature (e.g., approximately 37 degrees C.) and pressure (e.g., approximately 2 atm, 3 atm, etc.).

Any suitable acoustic parameters may be employed, depending on the sample to be treated. For example, the applied focused acoustic energy, pressure and/or temperature conditions may be lower when treating relatively fragile mammalian cells in contrast to the applied focused acoustic energy, pressure and/or temperature conditions when treating more robust organisms (e.g., bacteria, yeast) that require comparatively more energy to lyse. For example, mammalian cells are typically lysed by applying approximately 6 watts of focused acoustic energy for 1 minute; though, to cause yeast to release its DNA, in some cases, approximately 8 watts of focused acoustic energy may be applied for up to 3 minutes. Accordingly, cells within the solution may be lysed in a manner so as to release intracellular components therein, without damaging the molecules of interest.

To disrupt the molecular bonds of the intracellular components in a suitable manner, it may be preferable to subject the sample within the treatment area to a combination of processing conditions that varies from the conditions used to lyse the cells. As a result, the parameters of focused acoustic treatment may be adjusted accordingly, for example, the amount of focused acoustic energy used for molecular bond disruption may be less than the amount of focused acoustic energy used for cellular lysis.

In some embodiments, the vessel may be configured so as to allow for straight forward addition into and/or exchange of buffer with the sample solution. Any suitable buffer may be employed. For example, a buffer may contain enzymes such as proteinase, deoxyribonuclease (DNase), ribonuclease (RNase), or other components, for destabilizing and/or denaturing molecules (e.g., nucleic acids, proteins, etc.), in some cases, promoting adhesion of certain molecules to hydrophilic surfaces. Wash buffers may be employed, such as those that contain detergents and/or alcohols that, in some cases, may also promote adhesion to hydrophilic surfaces. In some embodiments, a neutral pH buffer may be used, for elution or washing of molecules from certain types of surfaces. In some embodiments, buffers may include one or more reactants (e.g., deoxynucleotides) and/or enzymes (e.g., polymerase) that may be used for synthetic and/or other chemical reactions (e.g., polymerase chain reaction).

In some embodiments, the movable walls may be re-positioned similar to that shown in FIG. 2, where an opening is provided for access to the treatment area. Here, a suitable buffer (e.g., sodium dodecyl sulfate based buffer, detergent, surfactant, etc.) may be added to the sample material, or an appropriate amount of existing solution within the treatment area may be removed therefrom. In some embodiments, relatively low concentrations of buffer, detergent and/or surfactant may be employed with sample materials processed within embodiments of vessels described herein, which may be beneficial for downstream analysis/processing (e.g., mass spectrometry).

The movable walls on either side of the treatment area may then be re-positioned for subsequent acoustic treatment. The parameters of acoustic treatment may be similar to those typically used in the art for disrupting intermolecular bonds, separating superfluous molecules from the particular molecules of interest, to be isolated and/or purified.

A similar re-configuration of the movable walls of the vessel may be performed so as to prepare the treatment area for a subsequent step of washing and purification of the molecules of interest. In some embodiments, a solid phase material, such as beads, that binds or adheres to certain molecules of the sample, along with an optional additional liquid reagent to further promote binding, may be added to the treatment area, for example, via a suitable port. In some cases, a frit or filter may be embedded or attached to the movable walls, or positioned at a region of the wall of the vessel, and the solid phase material to which molecules may bind may be embedded within the frit/filter. The frit or filter may be selectively permeable to gases or liquids, but not solid particles over a threshold size.

The sample may be suitably mixed with the solid phase material, for example, by applying focused acoustic energy, resulting in suitable binding of the molecules of interest thereto. Wash fluids may be added to the treatment area, for example, by moving walls within the vessel to open one or more appropriate ports. Accordingly, portions of the sample that are not bound to the solid phase material may be washed from the treatment area. Subsequently, the molecules of interest may be eluted by adding an appropriate liquid reagent that causes the molecules to be released from the solid phase material.

Alternatively, some of the molecules of interest, or a solid phase (e.g., beads, other objects, etc.) to which the molecules adhere to or are attached, may have magnetic properties or are otherwise susceptible to manipulation from a magnetic field. For some embodiments, the system may include a magnet movably positioned adjacent (e.g., external) to the vessel. Accordingly, by moving the magnet, the magnetic field may be manipulated or altered so as to cause the magnetically susceptible molecules to move toward a preferred region, for collection or further processing thereof.

The vessel may be able to accommodate any suitable volume of sample material. In some embodiments, the sample material has a volume of between 1 microliter and 500 microliters, between 10 microliters and 500 microliters, between 50 microliters and 300 microliters, or between 100 microliters and 200 microliters (e.g., approximately 100 microliters). The vessel may be constructed to accommodate sample material having volumes outside of these ranges.

As discussed above, reduction of the volume of the treatment area and/or sample material may be effective to increase the pressure of the sample material. Though, other methods may be used for pressurizing the sample material. In some embodiments, a gas-line device may engage with and pressurize the chamber. For example, the vessel may include a pressurization inlet (not shown in the figures) through which a fluid (e.g., inert gas or liquid) may be forcibly injected to pressurize the internal volume of the chamber and/or treatment area. Such methods may be applicable for portions of an acoustic treatment system other than a treatment area, for example, the coupling medium as well.

In some embodiments, pressure may be applied to the sample or to the coupling medium that transmits acoustic energy, for example, by pressurizing the fluid, to improve acoustic coupling between the acoustic energy source and the sample. Or, the sample within an interior space of a vessel may be pressurized relative to standard atmospheric pressure (e.g., to 2, 3, 4, or more atmospheres of pressure) to improve sample processing. When focused acoustic energy is subsequently applied to the sample, the desired result may be obtained in a shorter time period and/or, in some applications, may also result in improved sample processing and output quality (e.g., suitably sterilized, fragmented, homogenized, etc.).

In some cases, without wishing to be bound by theory, by increasing the pressure to which the sample is subjected, the acoustic energy dose required to cavitate portions of the sample (e.g., liquid, solution) may be greater. This may increase the shear forces consequent to cavitation bubble collapse. This may also result in greater retention time of the sample in the focal zone of the applied acoustic field and/or reduced rate of sample escaping the focal zone. This in turn may effectively increase the collision frequency of the sample with the acoustic bubbles generated by the applied energy and/or increase their resultant shear forces upon bubble collapse.

In some cases, it is possible that pressurization of the sample during ultrasonic treatment may effect a transient increase in the effective viscosity of the sample, and that the acoustic energy has a greater effect in this altered state. This increase in effective strength may result in the observation of finer particle formation, faster tissue homogenization, accelerated lysis of microbial organisms or cells, more effective sterilization of the sample, or otherwise provide for increased precision or speed of processing using the acoustic energy treatment process.

In some cases, acoustic treatment of a sample causes cavitation or other disruption in the sample such that energy that would otherwise be directed to processing sample material is absorbed, reflected or otherwise wasted or left unused for processing the sample. For example, cavitation or other relatively violent motion in a sample caused by acoustic energy can cause a portion of a sample to be ejected from the sample and into other areas of a vessel holding the sample, such as on the vessel sidewall. Time spent by the ejected sample portion outside of an acoustic focal zone or other area where the sample portion can be subjected to suitable acoustic energy may cause the sample to be incompletely or otherwise improperly processed or result in a process that requires more time and/or energy than necessary to achieve the desired result. Indeed, in some cases, ejected sample material may stick to a vessel sidewall or other location outside of the main sample volume, thus resulting in the ejected material not be acoustically processed at all. Embodiments of the present disclosure provide for an enclosed environment through which such energy loss may be alleviated.

In some embodiments, the pressure of the treatment area may be monitored and set to a preferred value or range. As noted above, the relative position of the movable wall(s) within the vessel may be adjusted to increase or decrease the pressure of the treatment area. In actuating the movable wall(s), an appropriate amount of force may be applied to the treatment area. This force may be applied via any suitable arrangement. In some embodiments, springs, other biasing elements and/or weights may be coupled to the movable wall(s), for providing a desired force for pressurizing the treatment area. Or, a force transducer may be employed via a closed loop control system to keep the force applied to the wall within a desired range.

Figure 5A:
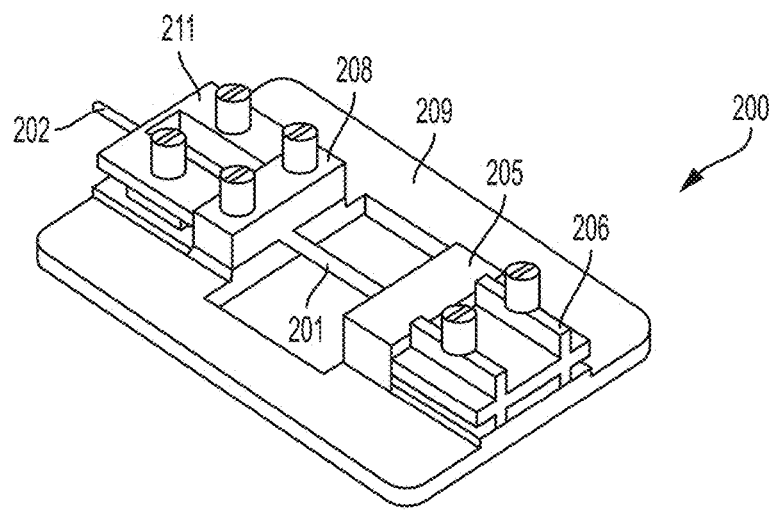
FIGS. 5A-5C depict an acoustic treatment system in accordance with an embodiment.
Figure 5B:
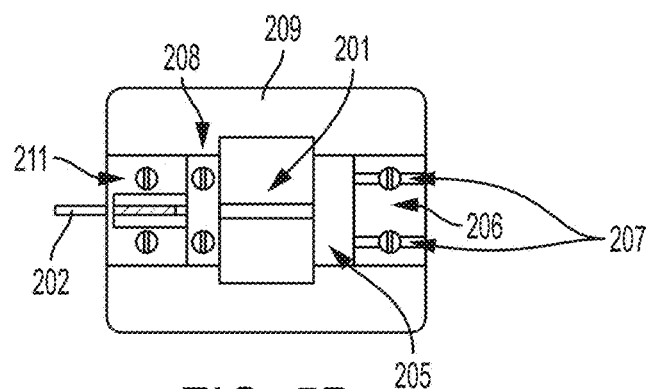
Figure 5C:
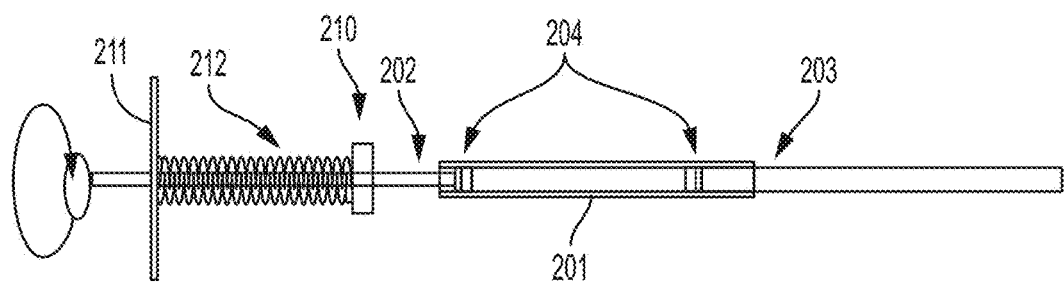

FIGS. 5A-5C respectively illustrate a perspective view, a top view and a side view of an example of an assembly 200 including a vessel for holding a sample, for suitable processing thereof. The assembly 200 may have one or more movable walls that are arranged to manipulate the sample such that the effects of focused acoustics may be enhanced. For example, the movable wall(s) may be actuated so as to apply a desired amount of pressure to the treatment area.

The assembly 200 includes a vessel 201 and movable walls, provided as pistons 202, 203 located on opposite ends of the vessel, the pistons enclosing the treatment area where sample material is processed (e.g., exposed to focused acoustic energy). In this example, the vessel 201 is provided as a cylindrical glass tube having an inner diameter of approximately 3.65 mm and a wall thickness of approximately 0.8 mm. The pistons 202, 203 are provided as nylon plungers, each having an outer diameter shaped similarly to, yet slightly smaller than the inner diameter of the wall of the vessel 201. The pistons 202, 203 further include a groove cut to accommodate corresponding O-rings 204, which provide respective sealing for preventing undesirable leakage to or from the treatment area.

As shown, the vessel 201 and pistons 202, 203 are coupled to a base plate 209, which has a receiving block 205 sized and shaped to receive and secure the vessel and pistons, as desired. Here, the piston 203 extends through a suitable opening of the receiving block 205, and a clamp 206 with fasteners 207 (e.g., thumb screws) secures the piston in place. The other piston 202 is secured at the opposite end of the vessel 201 via clamps 208, 211, each having respective fasteners and openings through which the piston 202 extends.

In this example, the exterior surface of the piston 202 is threaded (threads not expressly shown in the figures) such that a nut 210 having an interior surface with complementary threads can be coupled therewith. The nut 210 is situated within a compartment of the clamp 208 which is, in turn, structured to hold the nut 210 in place during rotation of the piston 202 relative to the nut 210. That is, the outer diameter of the nut 210 extends outward a sufficient amount such that the clamp 208 impedes rotational movement of the nut 210 relative to the clamp 208 and base plate 204. Accordingly, rotation of the piston 202 causes relative movement of the piston 202 through the nut 210, as determined by the complementary threaded structure.

A spring 212 is further positioned over the piston 202 and retained between the nut 210 and a wall of a clamp 211. The clamp 211 is secured to the base plate 204 and, while the opening of the clamp 211 is sized to permit the piston 202 to pass through, the opening is not large enough to accommodate extension of the spring 212 therethrough. As shown, the nut 210 and the wall of the clamp 211 serve as barriers on opposite ends of the spring 212, holding the spring 212 in place.

The spring 212 may be compressed or extended by a suitable method. For example, the piston 202 may be rotated in a manner so as to cause the nut to translate along the threads in a direction away from the vessel 201, resulting in compression of the spring 212. Or, alternatively, the piston 202 may be rotated such that the wall of the clamp 211 is advanced further toward the vessel 201, also causing spring compression. Such spring compression may, in turn, provide a compressive force to the treatment area of the vessel 201, resulting in an overall pressure, based on the area of the inner diameter of the vessel. Depending on the degree to which the spring is compressed, different forces and, hence, pressures, may be applied to the treatment area.

It can be appreciated that other arrangements may be employed. For example, appropriate force may be applied to one or both of the pistons using springs, weights, motors and/or a closed loop feedback system having force transducers or other actuating/sensing members.

Using the assembly 200 shown in FIGS. 5A-5C, the effect of mechanically-applied pressure on the shearing of DNA resulting from the exposure of focused acoustic energy was observed. Here, 100 microliters of lambda DNA (greater than or equal to 10 Mbp in length), at a concentration of 31 microgram/mL, was loaded into the vessel 201. The assembly 100, including the vessel 201 holding the sample material, was placed in the water bath of a Covaris E220 AFA instrument configured such that the focal point of acoustic energy is entrained at the center of the vessel 201. A hydrophobic Teflon cylinder (approximately 1 mm in diameter and 13 mm in length) was also supplied to the vessel, effectively lowering the nucleation threshold for cavitation within the treatment area. Samples were then subject to suitable focused acoustic treatment (e.g., peak incident power of 175 Watts, duty factor of 10%, cycles per burst of 200, treatment time of 180 seconds) appropriate for shearing DNA to a median of 215 bp, under various pressures (i.e., 1 atm, 2 atm, 3 atm above the ambient pressure) applied to the treatment area.

Figure 6:
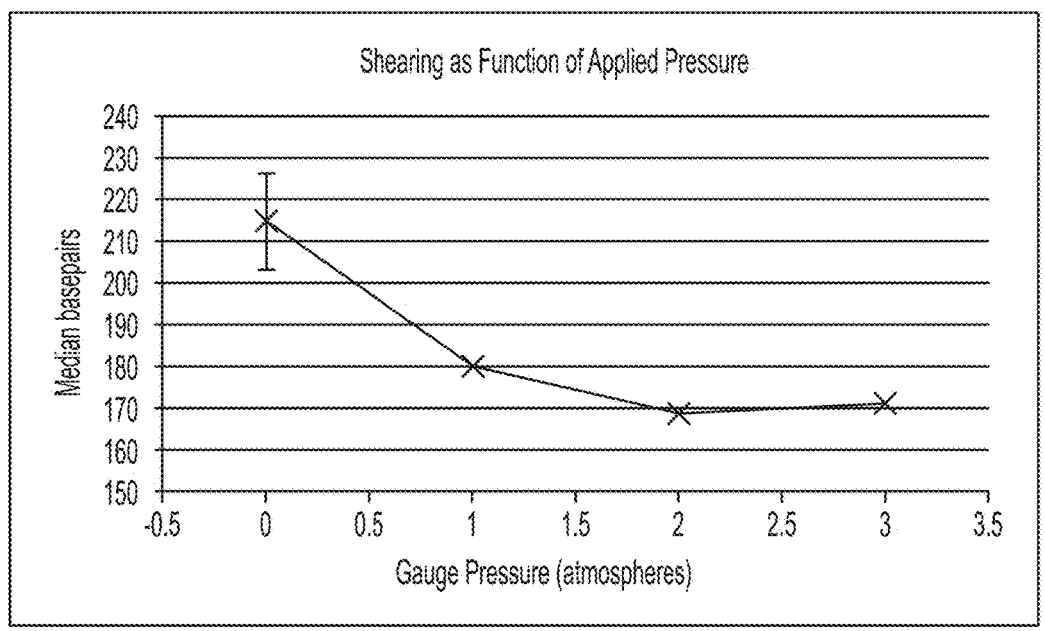
FIG. 6 shows results of acoustic processing with applied pressure using the system of FIGS. 5A-5C.

FIG. 6 shows the resulting median base pair values of the sheared DNA according to the amount of atmospheric pressures above the ambient pressure. That is, for example, the applied pressure of 0 atm shown in FIG. 6 indicates focused acoustic processing having occurred at ambient pressure (i.e., approximately 1 atm), and the applied pressure of 1 atm in FIGS. 6 indicates focused acoustic processing having occurred at 1 atm above the ambient pressure (i.e., approximately 2 atm). As shown, the median base pair value was observed to decrease with increasing pressure applied to the treatment area, which indicates that DNA is sheared to a greater degree when subject to focused acoustic energy under higher than ambient pressure. For instance, without additional pressure applied to the treatment area during focused acoustic treatment, DNA within the sample was observed to shear to a median of 215 bp; though, when an additional 2-3 atm of pressure was applied to the treatment area during focused acoustic treatment, DNA within the sample was observed to shear to a median of 170 bp. Without wishing to be bound by theory, it is thought that the increase in pressure within the treatment area during acoustic treatment effectively increases the degree to which the sample is exposed to the focused acoustic energy, hence, increasing overall efficiency of the process. In addition, it has been found that such acoustic energy loss or waste can be caused by gas present in the sample interfering with the acoustic energy. Accordingly, it has been discovered that acoustic energy loss or otherwise inefficient acoustic processing can be substantially reduced by lowering the amount of gas that can be absorbed, dissolved or otherwise incorporated into a liquid portion of a sample. Without wishing to be bound to any particular theory, it is thought that acoustic processing of a sample that includes liquid, particularly at relatively higher energy levels, tends to disrupt the interface between the sample and a gas above the sample. This disruption, which in some cases may include turbulent motion at the interface, may cause transfer of gas into the sample liquid (e.g., such as by dissolution or other mechanism). Gas carried by the sample liquid (e.g., whether dissolved and/or in bubble form) may interfere with acoustic processing, such as by gas bubbles reflecting acoustic energy, an increase in gas bubbles present in the sample caused by release of dissolved gas from the liquid, increased pressure in collapsing cavitation bubbles reducing energy that would otherwise be directed to sample material, and/or potentially other mechanisms.

In further embodiments of the present disclosure, the coupling medium through which acoustic energy is transmitted may be flexible, having the ability to be deformed toward the vessel upon an application of pressure thereto. When using a typical coupling medium for focused acoustic energy processing of a sample held within a vessel, bubbles (e.g., gas carried by the sample liquid), particles, or other defects may detrimentally influence the overall quality of results of the acoustic energy treatment. For instance, the presence of such interfaces/defects along the path of acoustic travel may affect (e.g., reflection, absorption, deflection, etc.) the level of acoustic energy that ultimately reaches the sample material, diminishing the impact of the acoustic energy. If the presence of such interfaces between the acoustic energy source and the sample material is minimized or otherwise reduced, then the effects of overall acoustic energy treatment may be more favorable.

In various embodiments, when the coupling medium is deformed so as to push or press up against the vessel, the amount of defects that would otherwise be present along the path through which the acoustic energy travels may be reduced. That is, by having the coupling medium form a tighter connection with the vessel, the tendency for the acoustic energy to be deflected in a way that lessens its efficacy is lessened. FIGS. 7-12 depict various illustrative embodiments where a flexible coupling medium is employed in an acoustic treatment system.

In FIGS. 7-10, an acoustic treatment system 100 includes a coupling medium container 15 that holds a coupling medium 16 therein. The container 15 includes a vessel holder 18 for holding a vessel containing a sample material in a suitable position so that the sample material may be exposed to acoustic energy. An acoustic source 14 is suitably positioned so as to direct acoustic waves toward the vessel held by the vessel holder 18.

In this embodiment, the vessel holder 18 is provided as a surface upon which a vessel may reside, however, other arrangements may be possible. For example, the vessel holder 18 may have a recessed area or adhesive region for receiving a suitable vessel and maintaining the vessel is an appropriate position for acoustic treatment.

In various embodiments, the coupling medium 16 is flexible so as to be deformable upon the application of pressure thereto. In some embodiments, the coupling medium includes a fluid (e.g., water, buffer solution, air, non-aqueous liquids, silicone oil, etc.) and a deformable material, such as a flexible membrane, that at least partially surrounds or otherwise encloses the fluid. For example, the coupling medium may be provided as a bladder-type arrangement. In some embodiments, the coupling medium includes a flexible membrane completely surrounding the fluid, similar to that of a bladder, balloon, bag, or other similar configuration. In other embodiments, the coupling medium is provided as a flexible membrane that is disposed adjacent to and covering a fluid reservoir.

As shown in FIGS. 7-10, the fluid portion of the coupling medium 16 is held within the container 15, and a flexible membrane 20 is provided between the fluid and the vessel location. The flexible membrane 20 may provide a covering for suitable protection of the fluid portion of the coupling medium, for example, keeping the fluid from spilling out of the container 15 or preventing contamination thereof, while also permitting the coupling medium to alter its shape in a controlled manner.

Figure 7:
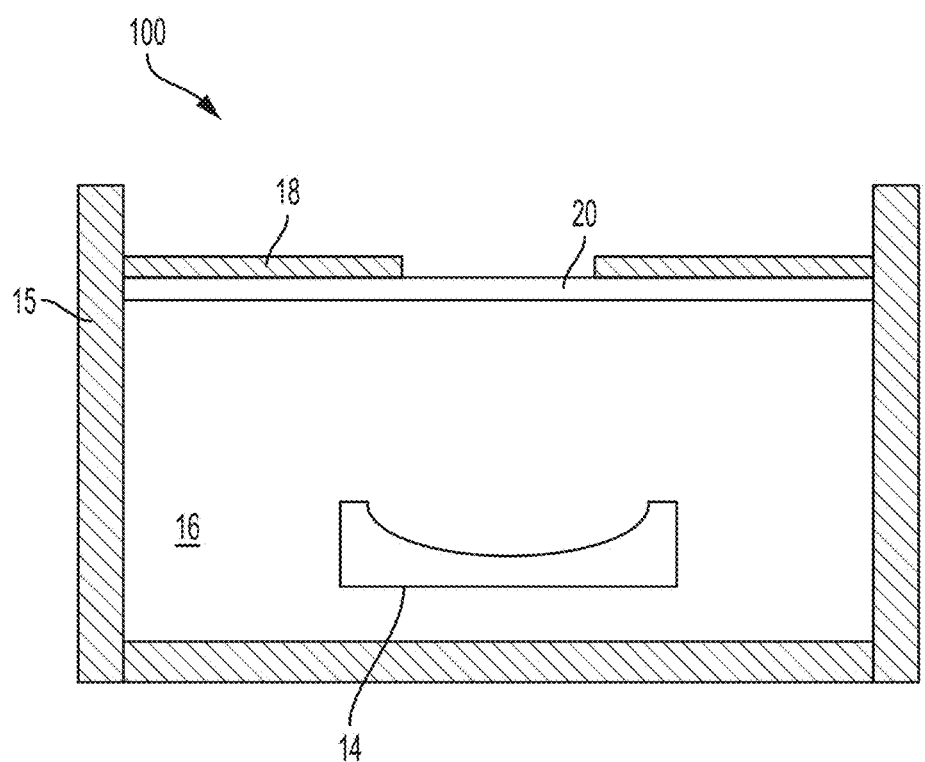
FIG. 7 illustrates a schematic of a cross-sectional view of an acoustic treatment system in accordance with an embodiment.

FIG. 7 shows the system 100 prior to application of pressure to the coupling medium 16. As shown, the coupling medium 16 rests within the confines of the container 15, with the membrane 20 suitably enclosing the fluid portion of the coupling medium.

Figure 8:
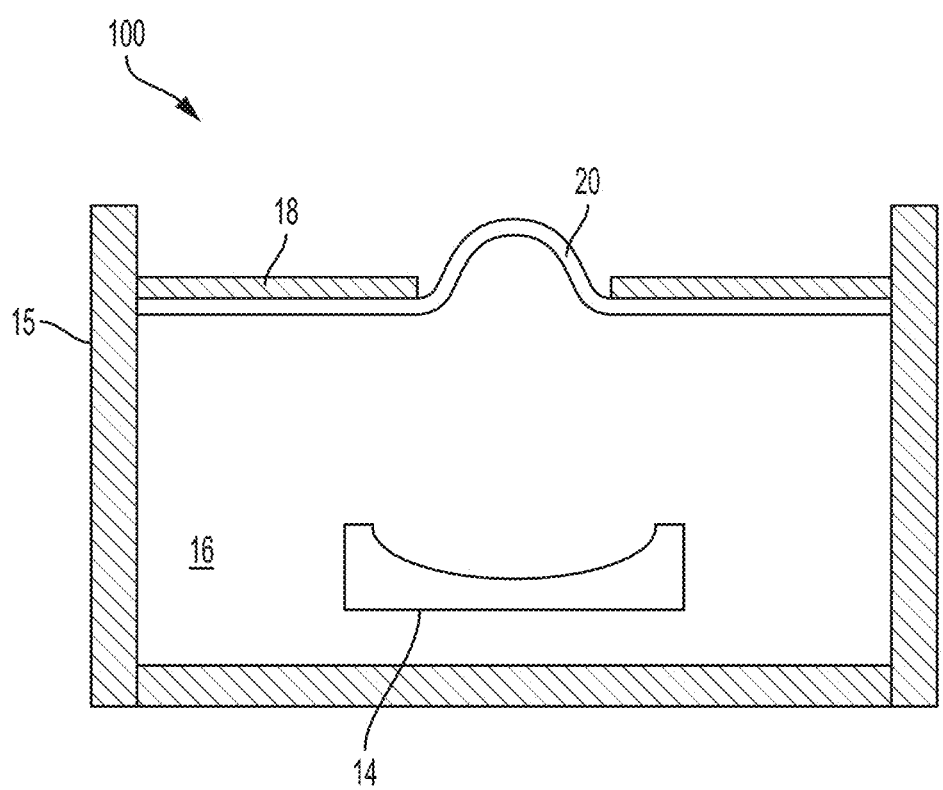
FIGS. 8-10 show the system of FIG. 7 in use.

In FIG. 8, the coupling medium 16, including the flexible membrane 20 is deformed so as to protrude outward toward the region where the vessel holder 18 holds a vessel containing sample material. In some embodiments, a positive pressure is applied to the coupling medium 16, for example, via a pressure inlet (not shown in the figures).

In some cases, the application of pressure may result in the elimination of air pockets, other gas, or defects/interfaces that may be present within the coupling medium 16. In other embodiments, focused acoustic energy emitted from the acoustic energy source 14 may cause the pressure of the coupling medium 16 to increase. Alternatively, pressure may be applied by physical contact to the coupling medium 16. For example, one or more walls of the container 15 may be moved inward so as to push against the coupling medium 16, applying a compressive pressure thereto. As a result, in this embodiment, the coupling medium 16, including coupling fluid and flexible membrane 20, may be pushed outward toward the vessel location. It can be appreciated that any suitable method may be used to apply pressure to the coupling medium 16, as the present disclosure is not limited to any of the particular examples described above.

Figure 9:
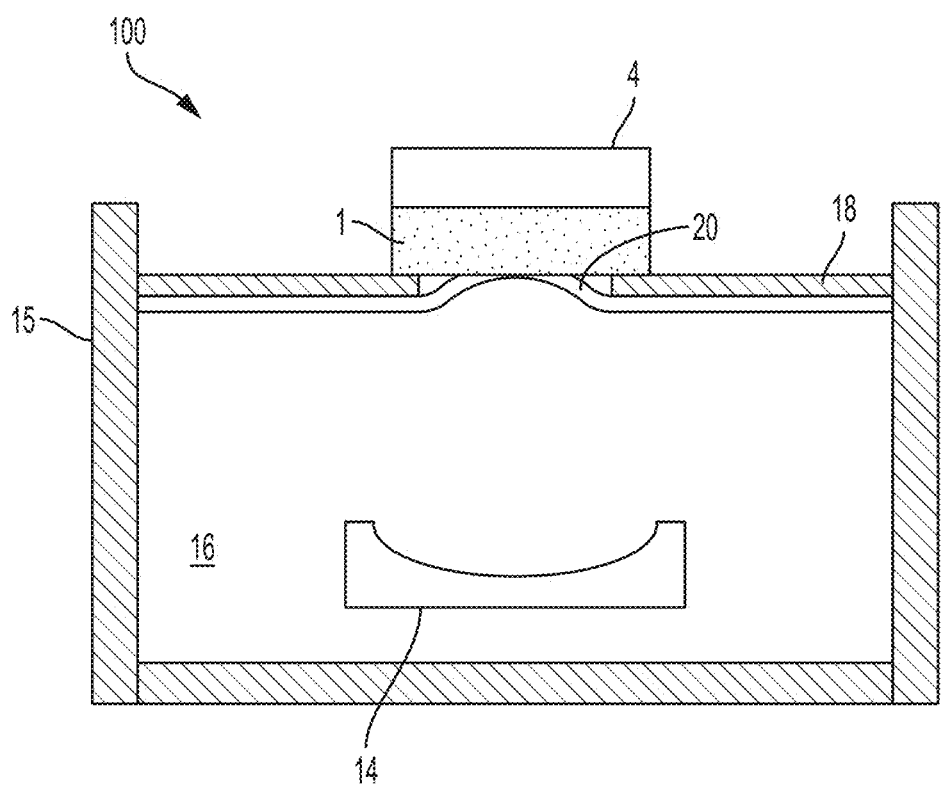

In FIG. 9, a vessel 4 containing a sample material 1 is placed on the vessel holder 18 in a position suitable for acoustic treatment. Here, while under pressure, the flexible coupling medium 16 presses up against the exterior wall of the vessel 4. Accordingly, as shown, a tight interface is formed between the vessel 4 and the flexible membrane 20 such that the amount of defects that would deflect, reflect or otherwise interfere with the transmission of acoustic energy to the sample material 1 is reduced.

Figure 10:
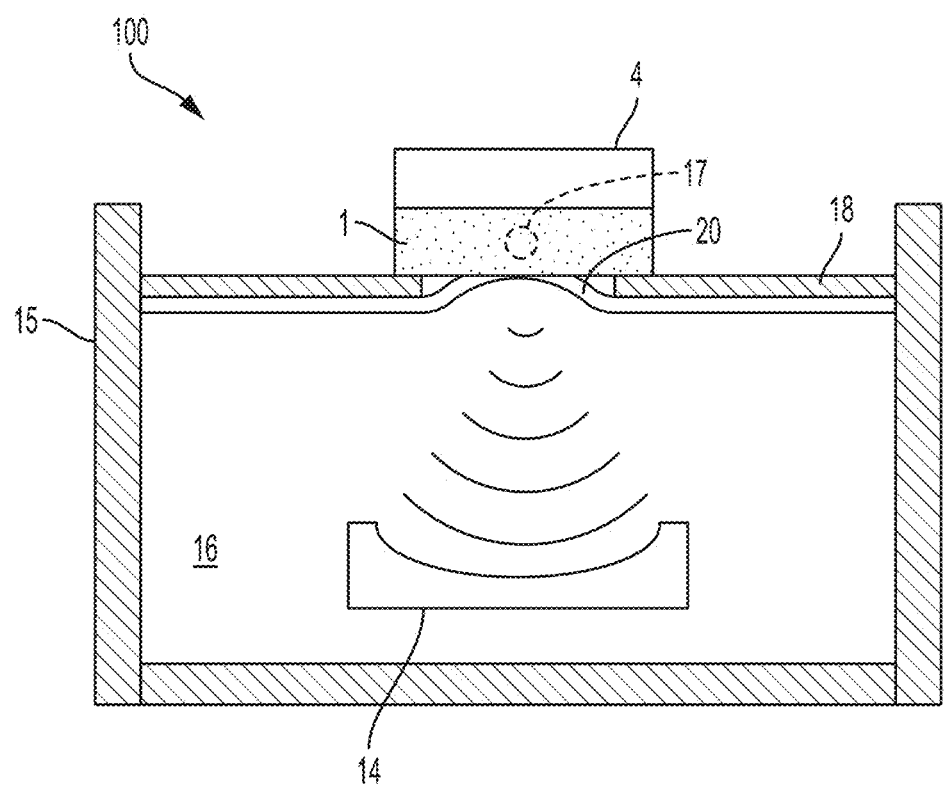

In FIG. 10, the acoustic energy source 14 is operated to create an acoustic focal zone 17 within the vessel 4 so as to suitably process the sample material 1 located therein. Here, the acoustic wavetrain travels through the fluid portion of the coupling medium 16, through the flexible membrane 20, through the chamber wall of the vessel 4 and forms the focal zone 17 at the sample material 1. This focused acoustic energy has a stronger throughput or energy level than would otherwise be the case if the coupling medium 16 were not deformed in the manner as discussed above.

Figure 11:
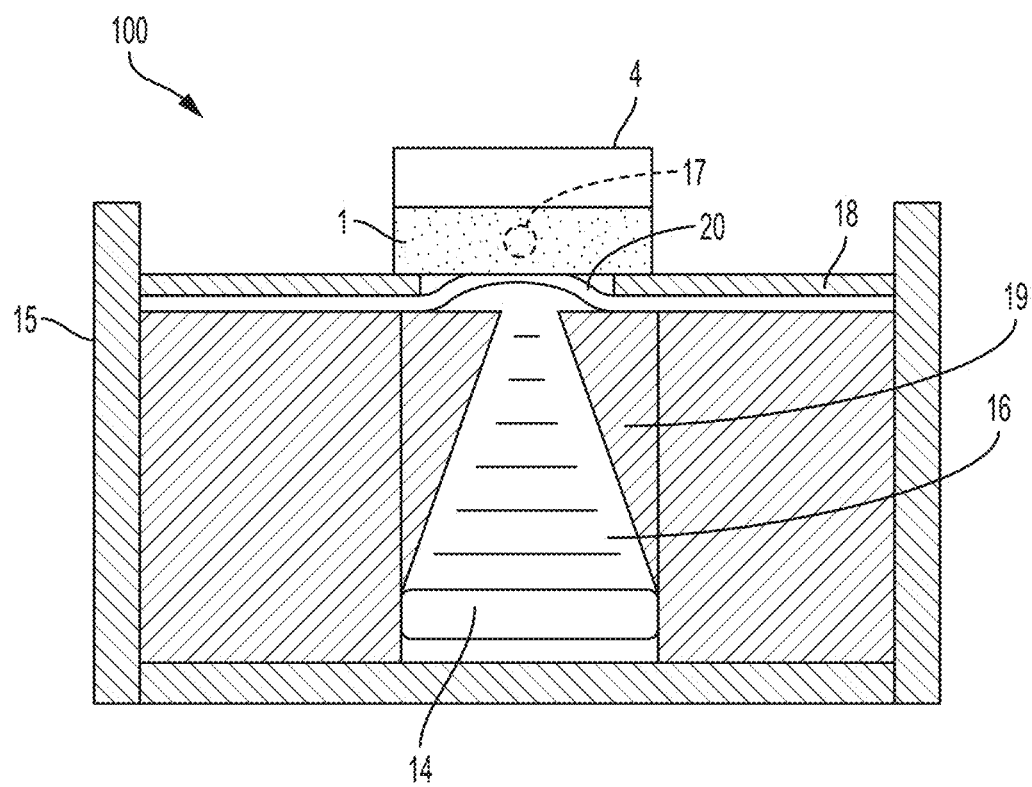
FIG. 11 depicts a schematic of a cross-sectional view of another acoustic treatment system in accordance with an embodiment.

It can be appreciated that flexible coupling mediums described herein may be employed with any suitable acoustic treatment system. For example, FIG. 11 depicts another illustrative embodiment of an acoustic treatment system 100 that includes an acoustic transducer that emits an unfocused or otherwise non-convergent acoustic wave (e.g., generated from an acoustic transducer having a relatively flat surface from which acoustic energy is emitted) in cooperation with a waveguide 19 to form a suitable focal zone 17 of acoustic energy within the vessel 4. In this embodiment, the waveguide 19 has an inner wall having a tapered shape such that acoustic energy which impinges against the wall is redirected or otherwise reflected in a manner so as to form the focal zone of acoustic energy in a suitable manner. Various systems and methods of employing a waveguide to directed unfocused or non-convergent acoustic waves are described in U.S. application Ser. No. 14/101,855 entitled "Method and System for Acoustically Treating Material," aspects of which may be used in association with aspects of the present disclosure.

FIG. 11 illustrates a cross-section of the acoustic treatment system 100 where the waveguide 19 defines a tapered volume having a substantially conical shape, though, it can be appreciated that any suitable shape may be employed (e.g., parabolic, elliptical, curved, etc.).

Further, the acoustic treatment system 100 may be oriented in such a manner that reduces the presence of defects or interfacial effects along the path of acoustic wave travel. For example, there may be a tendency for bubbles 30 or particles 32 to accumulate or otherwise be present along the acoustic wave path.

Figure 12:
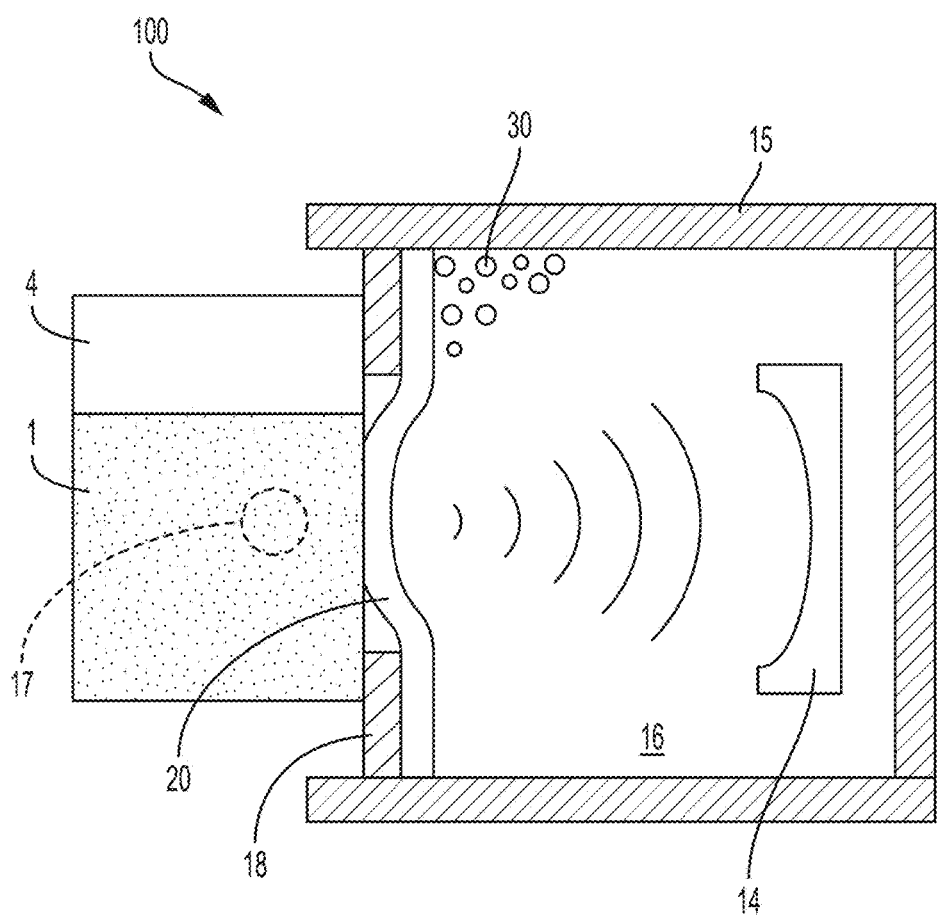
FIG. 12 shows a schematic of a cross-sectional view of an acoustic treatment system in accordance with an embodiment.

FIG. 12 depicts an illustrative embodiment of an acoustic treatment system 100 that is oriented so as to lie horizontally. In this embodiment, the acoustic energy source 14 emits acoustic waves in a lateral, or horizontal, direction toward the vessel interior. Here, bubbles 30 that might otherwise migrate toward the underside of the protrusion formed by the pressurized flexible membrane 20 move, by their buoyancy relative to the fluid of the coupling medium 16, away from the path of acoustic wave travel. Accordingly, the presence of gas may effectively be reduced at locations proximate to the vessel 4. It can be appreciated that the coupling medium may be deformed in any suitable direction (e.g., vertically, laterally, etc.), which may allow for defects (e.g., bubbles, particles, etc.) to move away from the path of acoustic wave travel.

In some embodiments, to reduce the amount of bubbles that may be located between the acoustic energy source and the vessel, it may be preferable to keep the space between the acoustic energy source and the flexible membrane substantially filled with coupling medium, to preclude entry or migration of bubbles or other defects. For example, where the coupling medium is provided in a bladder-type arrangement, the bladder may be kept full of the coupling medium so as to minimize or otherwise reduce the formation of bubbles. Or, the coupling medium may be treated, for example, via an applied pressure, with a suitable composition, etc., to maintain bubbles within a particular size range, or to reduce bubble formation altogether. For example, the application of pressure to the coupling medium may result in an overall reduction in size of bubbles therein.

The acoustic energy may be arranged in any suitable way, e.g., be sufficient to cause at least one of lysing, extraction, permeabilizing, stirring, catalyzing, degrading, fluidization, heating, particle breakdown, nucleic acid shearing, sterilization or disruption of molecular bonds in the sample. In some embodiments, the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A vessel for treating a material, comprising:
    a chamber defining an internal volume for containing a sample material and accommodating passage of the sample material to a treatment area;
    at least one opening for receiving an inflow of sample material into the treatment area or for discharging an outflow of material from the treatment area;
    a first wall movable within the internal volume of the chamber; and
    a second wall movable within the internal volume of the chamber, wherein the first and second walls, in cooperation, are adapted to cause the sample material to move within the internal volume and to adjust a pressure within the treatment area.

2. The vessel of claim 1, wherein at least one of the first wall and the second wall is configured for movement between a first position to permit flow of sample material into or out from the treatment area and a second position to obstruct flow of sample material into or out from the treatment area.

3. The vessel of claim 1, wherein the at least one opening includes an inlet for receiving an inflow of sample material into the internal volume, and an outlet separate from the inlet, for discharging the outflow of material from the internal volume.

4. The vessel of claim 1, wherein at least one of the first wall and the second wall forms a seal with an inner wall of the chamber.

5. The vessel of claim 1, wherein at least one of the first wall and the second wall includes a piston configured to move along a lateral direction of the chamber.

6. The vessel of claim 1, wherein the first and second walls, in cooperation, are adapted to cause an adjustment in volume of the sample material.

7. The vessel of claim 1, wherein the first and second walls, in cooperation, are adapted to cause an increase in pressure within the treatment area.

8. The vessel of claim 1, wherein the first and second walls are adapted to move the sample material toward or away from the at least one opening.

9. The vessel of claim 1, wherein at least one of the first wall and the second wall includes a hydrophobic material that faces toward the sample material.

10. The vessel of claim 1, wherein the internal volume of the chamber has a length of between 5 mm and 20 mm.

11. The vessel of claim 1, wherein the internal volume of the chamber has a width of between 0.1 mm and 5 mm.

12. The vessel of claim 1, wherein the sample material has a volume of between 1 microliter and 500 microliters.

13. A vessel for treating a material, comprising:
    a chamber defining an internal volume for containing a sample material and accommodating passage of the sample material to a treatment area, the chamber having a top side and extending in a lateral direction;
    at least one opening located at the top side of the chamber; and
    at least one wall movable within the internal volume of the chamber, configured for movement along the lateral direction between a first position to permit flow of sample material into or out from the treatment area and a second position to obstruct flow of sample material into or out from the treatment area.

14. The vessel of claim 13, wherein the at least one wall includes a first wall and a second wall, wherein the first and second walls, in cooperation, are adapted to cause the sample material to move within the internal volume and to adjust a pressure within the treatment area.

15. The vessel of claim 13, wherein the at least one opening includes an inlet for receiving an inflow of sample material into the treatment area, and an outlet separate from the inlet, for discharging the outflow of material from the treatment area.

16. The vessel of claim 13, wherein the at least one wall forms a seal with an inner wall of the chamber.

17. The vessel of claim 13, wherein the at least one wall includes a piston configured to move along a the lateral direction of the chamber.

18. The vessel of claim 13, wherein the at least one wall is adapted to cause an adjustment in volume of the sample material.

19. The vessel of claim 13, wherein the at least one wall is adapted to cause an increase in pressure within the treatment area.

20. The vessel of claim 13, wherein the at least one wall is adapted to move the sample material toward or away from the at least one opening.

21. The vessel of claim 13, wherein the at least one wall includes a hydrophobic material that faces toward the sample material.

22. The vessel of claim 13, wherein the internal volume of the chamber has a length of between 5 mm and 20 mm.

23. The vessel of claim 13, wherein the internal volume of the chamber has a width of between 0.1 mm and 5 mm.

24. The vessel of claim 13, wherein the sample material has a volume of between 10 microliters and 500 microliters.

25. A method of treating a material with acoustic energy, comprising:
causing flow of sample material into an internal volume of a chamber;
moving a first wall and a second wall in cooperation within the internal volume of the chamber to cause the sample material to move within the internal volume and to adjust pressure within a treatment area;
treating sample material located within the treatment area with acoustic energy having a frequency of about 100 kHz to 100 MHz and a focal zone of acoustic energy in the treatment area, the acoustic energy transmitted from an acoustic energy source to the chamber through a coupling medium held in a vessel; and
causing flow of the treated sample material away from the internal volume of the chamber.

26. The method of claim 25, wherein causing flow of sample material toward the internal volume of the chamber includes flowing the sample material into the internal volume through an inlet.

27. The method of claim 25, wherein causing flow of treated sample material away from the internal volume of the chamber includes flowing the sample material out of the internal volume through an outlet.

28. The method of claim 25, wherein moving the first and second wall in cooperation includes forming a seal with a wall of the chamber.

29. The method of claim 25, wherein moving the first and second wall in cooperation includes adjusting a volume of the sample material.

30. The method of claim 29, wherein moving the first and second wall in cooperation includes reducing a volume of the sample material.

31. The method of claim 29, wherein moving the first and second wall in cooperation includes increasing the pressure within the treatment area.

32. The method of claim 25, further comprising causing flow of an additional sample material into the internal volume of the chamber.

33. The method of claim 25, further comprising adjusting one or more parameters of the acoustic energy based on treatment of the sample material.

34. The method of claim 25, wherein treating the sample material with acoustic energy occurs simultaneously with moving of the sample material.

35. The method of claim 25, wherein treating the sample material with acoustic energy occurs when the pressure within the treatment area is greater than a pressure outside of the chamber.

36. The method of claim 25, wherein treating the sample material with acoustic energy occurs when the pressure within the treatment area is less than a pressure outside of the chamber.

37. The method of claim 25, wherein treating the sample material with acoustic energy includes exposing a biological material to focused acoustic energy.

38. A system for acoustically treating a material, comprising:
a vessel holder for holding a vessel having a chamber defining an internal volume for containing a sample material;
an acoustic energy source arranged to be spaced from the vessel and adapted to emit acoustic energy having a frequency of about 100 kHz to 100 MHz to create a focal zone of acoustic energy in the internal volume; and
a flexible coupling medium arranged to transmit acoustic energy from the acoustic energy source to the vessel and adapted for at least a portion to be deformed toward the vessel upon pressure application.

39. The system of claim 38, wherein the flexible coupling medium includes a bladder having a deformable material enclosing a fluid.

40. The system of claim 38, wherein a portion of the flexible coupling medium is adapted to press against a wall of the vessel upon application of pressure to the flexible coupling medium.

41. The system of claim 38, wherein the flexible coupling medium is configured such that, upon application of pressure to the flexible coupling medium, acoustic reflections of the transmitted acoustic energy between the acoustic energy source and the vessel are reduced.

42. The system of claim 38, wherein the flexible coupling medium is configured such that, upon application of pressure to the flexible coupling medium, the presence of gas is reduced at a location proximate to the vessel.

43. A method of treating a material with acoustic energy, comprising:
deforming a flexible coupling medium toward a vessel location;
positioning a vessel having a chamber defining an internal volume for containing a sample material at the vessel location; and
transmitting acoustic energy having a frequency of about 100 kHz to 100 from an acoustic energy source through the coupling medium to form a focal zone of acoustic energy within the internal volume.

44. The method of claim 43, wherein deforming the flexible coupling medium includes applying pressure to the flexible coupling medium.

45. The method of claim 44, wherein the flexible coupling medium includes a bladder having a deformable material enclosing a fluid, and applying pressure to the flexible coupling medium includes pressurizing the fluid within the bladder.

46. The method of claim 43, wherein deforming the flexible coupling medium includes pressing a portion of the flexible coupling medium against a wall of the vessel.

47. The method of claim 43, wherein positioning the vessel at the vessel location includes pressing a wall of the vessel against a portion of the flexible coupling medium.

48. The method of claim 43, wherein deforming the flexible coupling medium includes reducing acoustic reflections of the transmitted acoustic energy between the acoustic energy source and the vessel.

49. The method of claim 43, wherein deforming the flexible coupling medium includes reducing an amount of air bubbles or defects between the acoustic energy source and the vessel location.

50. The method of claim 43, wherein transmitting acoustic energy from the acoustic energy source includes transmitting acoustic energy in a direction other than an upward vertical direction relative to the vessel.

51. The method of claim 43, wherein transmitting acoustic energy from the acoustic energy source includes transmitting acoustic energy in a substantially horizontal direction relative to the vessel.

* * * * *